(12) United States Patent
Novichenok et al.

(10) Patent No.: US 9,351,789 B2
(45) Date of Patent: May 31, 2016

(54) ADJUSTABLE CATHETER FOR OSTIAL, SEPTAL, AND ROOF ABLATION IN ATRIAL FIBRILLATION PATIENTS

(71) Applicant: MEDTRONIC ABLATIOIN FRONTIERS LLC, Minneapolis, MN (US)

(72) Inventors: Alex Novichenok, San Diego, CA (US); Reynaldo O. Cruz, National City, CA (US); Aaron R. Strunk, San Diego, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 151 days.

(21) Appl. No.: 13/906,419

(22) Filed: May 31, 2013

(65) Prior Publication Data

US 2014/0358143 A1    Dec. 4, 2014

(51) Int. Cl.
*A61B 18/04* (2006.01)
*A61B 18/14* (2006.01)
*A61B 18/00* (2006.01)

(52) U.S. Cl.
CPC ..... *A61B 18/1492* (2013.01); *A61B 2018/0016* (2013.01); *A61B 2018/00214* (2013.01); *A61B 2018/00267* (2013.01); *A61B 2018/00351* (2013.01); *A61B 2018/00577* (2013.01); *A61B 2018/00613* (2013.01); *A61B 2018/1467* (2013.01)

(58) Field of Classification Search
CPC ............... A61B 18/1492; A61B 18/14; A61B 2018/00577; A61B 2018/00267; A61B 2018/00214; A61B 2018/1465; A61B 2018/1475; A61B 2018/1405; A61B 2018/1435; A61B 2018/00351; A61B 2017/003; A61B 2017/00318; A61B 2017/2927; A61B 2017/22061
USPC ................ 606/41–48; 600/374, 381; 607/122
See application file for complete search history.

(56) References Cited

U.S. PATENT DOCUMENTS 4,660,571 A    4/1987    Hess et al.
5,836,947 A    11/1998   Fleischman et al.
(Continued)

FOREIGN PATENT DOCUMENTS

WO    2007001981 A2    1/2007

OTHER PUBLICATIONS

International Search Report and Written Opinion dated Aug. 4, 2014 for International Application Serial No. PCT/US2014/032352, International Filing Date: Mar. 31, 2014 consisting of 8 pages.

*Primary Examiner* — Ronald Hupczey, Jr.
*Assistant Examiner* — Khadijeh Vahdat
(74) *Attorney, Agent, or Firm* — Christopher & Weisberg, P.A.

(57) ABSTRACT

A device and method for treating a variety of tissue locations within a patient's body using a single device that includes an elongate body having a distal portion, a shaft rotatably and slidably disposed within the elongate body, and a first arm and a second arm each coupled to the elongate body distal portion. Retraction and rotation of the shaft transitions the each arm from a linear configuration to a radially expanded configuration in which each arm has an arcuate shape and lies in a plane that is substantially orthogonal to the elongate body longitudinal axis. Electrodes coupled to the arms are equidistant from the longitudinal axis of the elongate body in different radial directions when the device is in the radially expanded configuration. The electrodes are radially symmetrical about the shaft when the radially expanded configuration has a first diameter or a second diameter.

19 Claims, 9 Drawing Sheets

(56) References Cited

U.S. PATENT DOCUMENTS

| | | |
|---|---|---|
| 6,004,269 A | 12/1999 | Crowley et al. |
| 6,330,473 B1 | 12/2001 | Swanson et al. |
| 6,430,426 B2 | 8/2002 | Avitall |
| 7,850,685 B2 * | 12/2010 | Kunis et al. ............ 606/41 |
| 8,235,986 B2 | 8/2012 | Kulesa et al. |
| 2003/0093072 A1 | 5/2003 | Friedman |
| 2006/0089637 A1 | 4/2006 | Werneth et al. |
| 2007/0219546 A1 | 9/2007 | Mody et al. |
| 2008/0281312 A1 * | 11/2008 | Werneth et al. .......... 606/33 |
| 2008/0281313 A1 | 11/2008 | Fagin et al. |
| 2009/0131930 A1 | 5/2009 | Gelbart et al. |
| 2011/0172658 A1 | 7/2011 | Gelbart et al. |
| 2013/0109987 A1 | 5/2013 | Kunis et al. |

\* cited by examiner

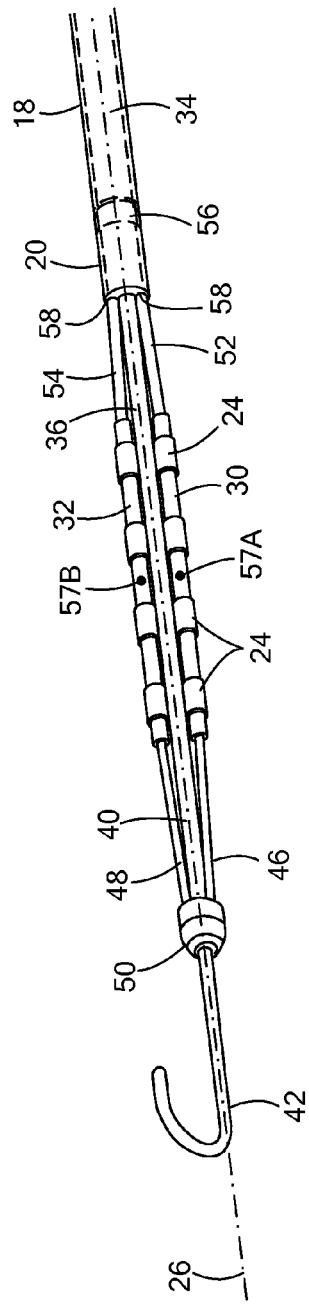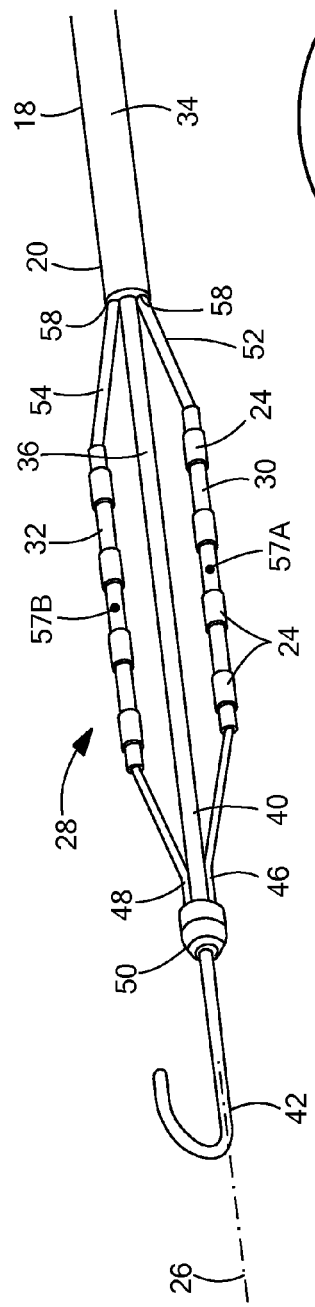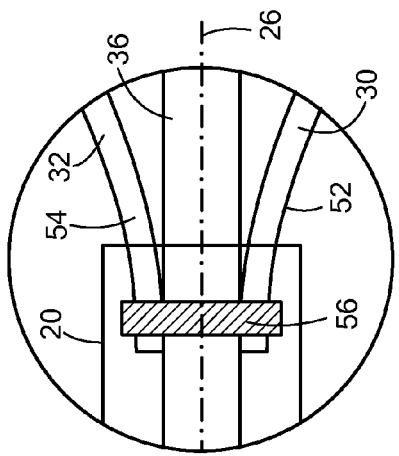

ADJUSTABLE CATHETER FOR OSTIAL, SEPTAL, AND ROOF ABLATION IN ATRIAL FIBRILLATION PATIENTS

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a device and method for treating a variety of tissue locations within a patient's body using a single device. In particular, the present invention relates to a device and method for thermally treating any or all of cardiac wall tissue, pulmonary vein ostia, pulmonary vein antra, and cardiac septal wall tissue with a medical device having an adjustable electrode array.

BACKGROUND OF THE INVENTION

Cardiac arrhythmia is term used to broadly describe a group of cardiac conditions involving abnormal electrical activity in the heart. In atrial fibrillation (AF), the most common type of cardiac arrhythmia, disorganized electrical impulses (usually generated by the roots of the pulmonary veins) interrupt the normal electrical impulses generated by the sinoatrial node, which in turn causes an irregular conduction of electrical impulses to the heartbeat-generating ventricles. AF may result from a number of conditions, such as hypertension, coronary artery disease, pericarditis, lung disease, hyperthyroidism, carbon monoxide poisoning, or rheumatoid arthritis.

Catheter ablation frequently used to treat AF, which involves a minimally invasive procedure by which areas of cardiac tissue that facilitate the irregular electrical conduction are ablated using any of a number of energy modalities. During catheter ablation, one or more pulmonary veins (PVs) may be targeted. AF is commonly initiated by foci located in the PVs. PVs are large blood vessels that carry oxygenated blood from the lungs to the left atrium (LA) of the heart. In order to disrupt the propagation of abnormal electrical currents, the ablation catheter is placed around the opening of the PV to the heart and/or within the PV where the foci are located. However, the PVs are usually not regularly shaped, and often have an asymmetrical interior that can be difficult to navigate. Further, the openings of two closely positioned PVs may form a single irregular opening, which can make ablation with many currently used ablation elements ineffective (for example, single loop-style ablation elements or the treatment elements of focal catheters). Additionally, the treatment of other types of cardiac arrhythmia may require ablation of tissue in or around the PV and tissue in other areas of the heart. However, it is often necessary to use more than one device in order to effectively destroy aberrant electrical currents. Having to replace a device during surgery can be time consuming, difficult to accomplish, and potentially dangerous for the patient.

Currently available devices may be used to treat conditions such as complex fractionated arterial electrograms (CFAEs), used for septal ablation, used to ablate pulmonary vein ostia, and used to create linear ablation lesions. Each of these devices is effective in ablating tissue, and each may be particularly suited to a certain area of anatomy. For example, some catheters may includes an electrode array that is well-suited for creating circumferential lesions about pulmonary vein ostia, whereas others do not include an expandable treatment element and are effective in creating linear lesions. As such, it may be necessary to use multiple ablation devices for treating a single atrial fibrillation patient, depending on the location(s) and number of aberrant electrical pathways that must be addressed.

Accordingly, an ablation device having one or more ablation elements suitable for treating aberrant electrical currents in a variety of cardiac locations is desired. In particular, the desired device is suitable for treating AF and other arrhythmias by ablating a variety of cardiac tissues, including the pulmonary veins, septum, and heart wall.

SUMMARY OF THE INVENTION

The present invention advantageously provides a device and method for treating a variety of tissue locations within a patient's body using a single device. In one embodiment, the device may generally include an elongate body including a longitudinal axis, a shaft rotatably and slidably disposed within the elongate body, a first arm including a distal end coupled to the shaft and a proximal end coupled to the elongate body, and a second arm including a distal end coupled to the shaft and a proximal end coupled to the elongate body. Retraction and rotation of the shaft may transition the first and second arms from a linear configuration to a radially expanded configuration in which each arm has an arcuate shape and lies in a plane that is substantially orthogonal to the elongate body longitudinal axis. The device may further include a first plurality of electrodes coupled to the first arm and a second plurality of electrodes coupled to the second arm. Each electrode may be equidistant from the longitudinal axis of the elongate body in different radial directions when the device is in the radially expanded configuration. Further, the electrodes may have a radial symmetry about the shaft. The elongate body may define a distal portion and a proximal portion and the shaft defines a distal portion and a proximal portion, the distal portion of the shaft extending distal of the distal portion of the elongate body. The device may further include a distal cap coupled to the distal portion of the shaft and the distal end of each of the first arm and second arm, each of the first arm and second arm having a midpoint that is equidistant from the distal cap and the distal portion of the elongate body. For example, the midpoint of the first arm and the midpoint of the second arm may be approximately 180° from each other in the plane that is substantially orthogonal to the elongate body longitudinal axis when the medical device is in the radially expanded configuration. The radially expanded configuration may include a diameter that is adjustable from a first diameter to at least a second diameter, the second diameter being greater than the first diameter. When the radially expanded configuration has a first diameter, the shaft may be rotated between approximately 45° and approximately 90° (for example, approximately 60°), such as by a rotational knob in a handle that is in communication with the proximal portion of the shaft. Further, when the radially expanded configuration has a second diameter, the shaft may be rotated less than approximately 45°.

In another embodiment, the device may generally include a first arm and a second arm each coupled to a distal portion of the medical device, the first arm and second arm each having a distal end and a proximal end, retraction of the distal ends of the first and second arm toward the proximal ends of the first and second arm transitioning the first and second arms from a linear configuration to a radially expanded configuration in which each arm has an arcuate shape and lies in a plane that is substantially orthogonal to the elongate body longitudinal axis. The medical device may define a longitudinal axis, the first arm includes a first plurality of electrodes and the second arm includes a second plurality of electrodes, each of the first and second plurality of electrodes being equidistant from the longitudinal axis of the medical device in different radial directions when the device is in the radially expanded configuration. The radially expanded configuration may have a diameter that is adjustable from a first diameter to at least a second diameter, each of the first and second plurality of electrodes being equidistant from the longitudinal axis of the medical device in different radial directions when the radially expanded configuration has a first diameter and when the radially expanded configuration has as second diameter.

The method may generally include transitioning a distal end of a medical device having a longitudinal axis from a linear configuration to a radially expanded configuration, the distal end of the medical device including a first arm having a plurality of electrodes and a second arm having a plurality of electrodes, the first arm and second arm lying along an axis that is parallel to the medical device longitudinal axis when the medical device is in the linear configuration, and the first arm and second arm lying in a plane that is substantially orthogonal to the medical device longitudinal axis when the medical device is in the radially expanded configuration. The radially expanded configuration may be adjustable between having a first diameter and having a second diameter. The method may further include activating the electrodes and creating an ablation lesion at any of a variety of locations within a patient's heart. For example, the method may include at least one of creating a linear ablation lesion on cardiac wall tissue, creating a circumferential ablation lesion on cardiac wall tissue, creating a circumferential ablation lesion about a pulmonary vein ostium, creating a circumferential ablation lesion about a pulmonary vein antrum, creating a circumferential ablation lesion within a pulmonary vein, and creating a lesion on cardiac septal wall tissue.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1B shows a device distal portion with adjustable electrode array in a first (linear) configuration;

FIG. 1C shows a device distal portion with adjustable electrode array in a first (linear) configuration with arms slightly spaced apart, so as to clearly illustrate device components;

FIG. 1D shows a close-up view of the point of connection between the first and second electrode arms and the shaft;

DETAILED DESCRIPTION OF THE INVENTION

Figure 1A:
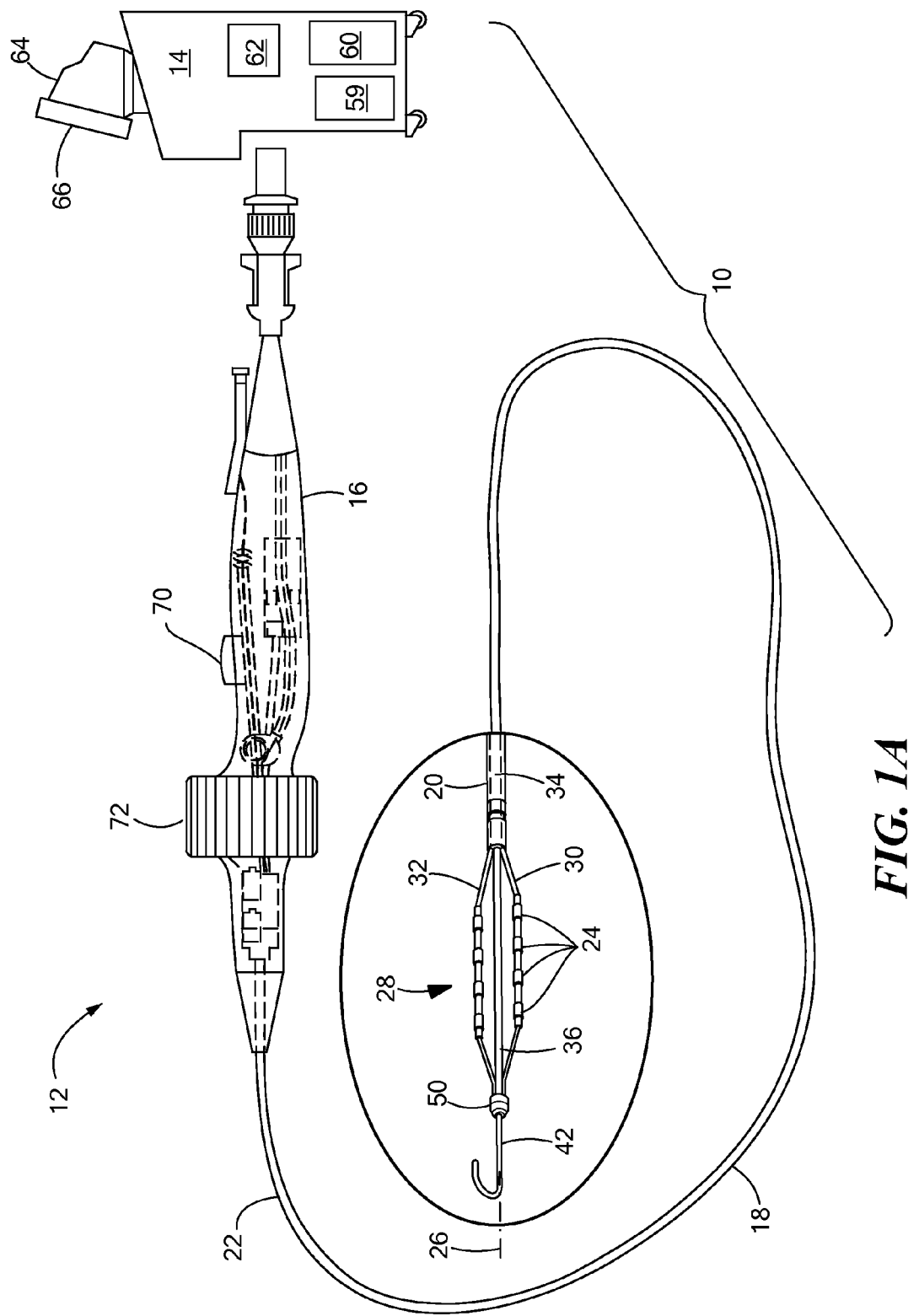
FIG. 1A shows a medical system including an ablation device with an adjustable electrode array.

Referring now to FIGS. 1A-1C, a medical system including an ablation device with an adjustable electrode array coupled to the distal end of the device is shown. The system 10 may generally include a medical device 12 for thermally treating or ablating an area of tissue, and a console 14 that houses various system controls. The system 10 may be adapted for use with a variety of energy modalities, including but not limited to, cryoablation, radiofrequency (RF) ablation, ultrasound ablation, microwave ablation, and laser ablation. For example, the system 10 shown in FIG. 1A may be suitable for use during RF ablation procedures.

Figure 5A:
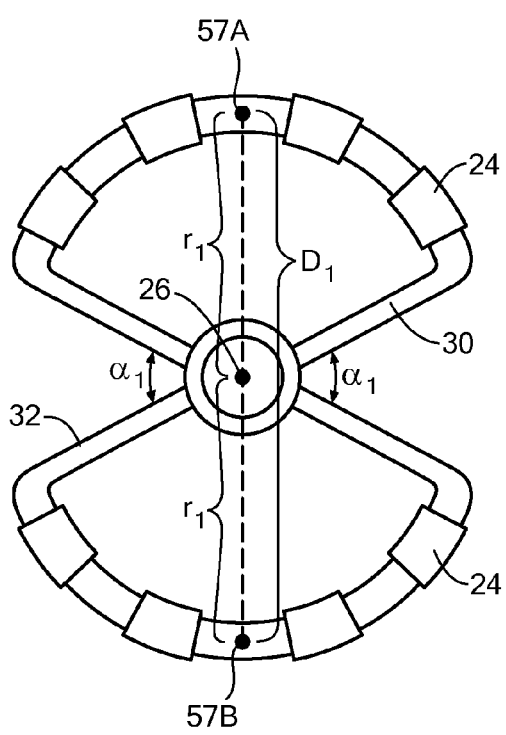
FIG. 5A shows an anterior view of an adjustable electrode array in a second (radially expanded) configuration.
Figure 5B:
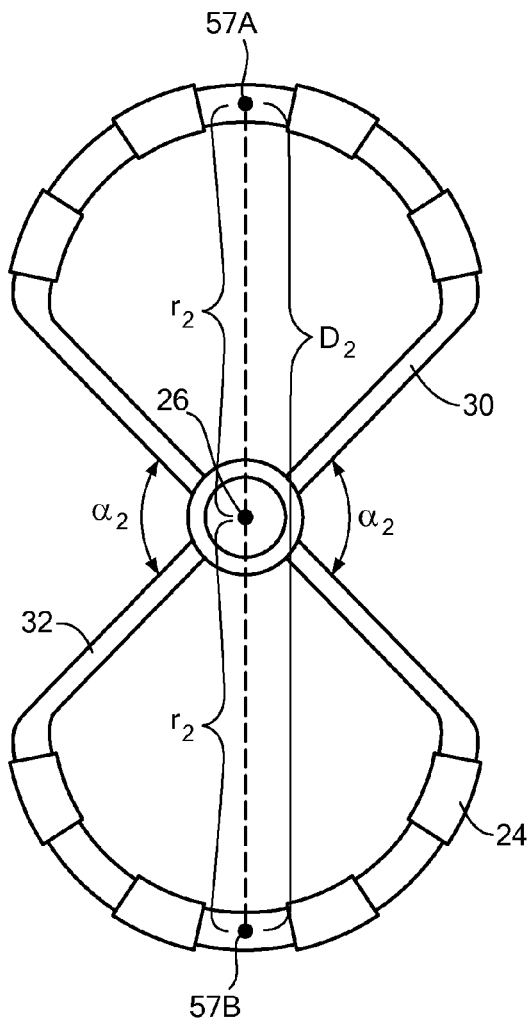
FIG. 5B shows an anterior view of an adjustable electrode array in a third (increased-diameter radially expanded) configuration.

The device 12 may generally include a handle 16, elongate body 18 having a distal portion 20 and a proximal portion 22, and one or more treatment elements 24 (for example, RF electrodes). The device 12 may have a longitudinal axis 26. The elongate body 18 may also have a longitudinal axis, which may be substantially coaxial with the device longitudinal axis 26. As shown in FIGS. 1A-1C, the distal portion 20 may include an electrode array 28 that is adjustable from a first (linear) configuration, as shown in FIGS. 1A-1C, to a variety of other configurations. For example, the adjustable electrode array may be transitionable from the first configuration to at least a second (radially expanded) configuration (as shown in FIGS. 3A-3C and 5A) and a third (increased-diameter radially expanded) configuration (as shown in FIG. 5B). The electrode array 28 may include a first electrode arm 30 (also referred to as "arm 30") and a second electrode arm 32 (also referred to as "arm 32"), each of which bearing a plurality of electrodes 24. For example, four electrodes 24 may be coupled to each arm 30, 32. The configuration shown in FIG. 1C is a linear configuration shown with the arms 30, 32 slightly spaced apart so as to better illustrate individual components of the device.

Each electrode 24 may be composed of a conductive or selectively conductive material and each electrode 24 may include a thermocouple (not shown). For example, the electrodes 24 may be composed of gold, which is nearly 4.5 times as thermally conductive as platinum. As a result, a gold electrode may maintain a more uniform temperature across the entirety of its surface area than a platinum electrode of the same dimensions. This allows for enhanced accuracy in temperature measurement, regardless of the thermocouple position. Each electrode 24 may be, for example, a band electrode that is affixed or otherwise coupled to an exterior surface of the arms 30, 32. Alternatively, each electrode may be an exposed portion of the arm 30, 32. That is, the arms 30, 32 may be coated with a layer of insulative material, which layer may be removed in certain areas to expose a conductive or selectively conductive material layered beneath the insulative material. These exposed areas are conductive (or selectively conductive) and function in the same manner as band electrodes. In addition or as an alternative to ablation, the electrodes 24 may be used for pacing and/or mapping cardiac tissue.

The elongate body 18 of the device 12 may include one or more lumens. As shown in FIGS. 1A-1C, elongate body 18 of the device 12 may include a main lumen 34 in which a shaft 36 is rotatably and slidably disposed. The longitudinal axis of the shaft 36 may be substantially coaxial with the device longitudinal axis 26. Further, the shaft 36 may include a guidewire lumen 40 in which a guidewire 42 is rotatably and slidably disposed. Thus, the device 12 may be referred to as an "over-the-wire" device. The distal end 44 of the shaft 36 and the distal end 46, 48 of each arm 30, 32 may be coupled together by a distal cap 50 that is atraumatic to the patient. The proximal end 52, 54 of each arm 30, 32 may be secured within the distal portion 20 of the elongate body 18. For example, the proximal end 52, 54 of each arm 30, 32 may be coupled to a cuff 56 having an aperture through which the shaft 36 may be extended, retracted, and rotated. Each arm 30, 32 may include a midpoint 57A, 57B that is substantially equidistant between the distal cap 50 and the point 58 at which the arms 30, 32 exit the elongate body 18. In other words, the midpoint 57A, 57B (shown in the figures as an imaginary dot) represents the middle point of the exposed portion of each arm 30, 32 not captured beneath the distal cap 50 or disposed within the elongate body 18.

If the device 12 is a cryoablation catheter, for example, the elongate body 18 may include a fluid injection lumen in fluid communication with a coolant reservoir 59, and a fluid return lumen in fluid communication with a coolant return reservoir 60. Depending on the energy modality being used, the lumens of the elongate body 18 may be in fluid communication with any of a number of fluids, such as saline. In some embodiments, one or more other lumens may be disposed within the main lumen, and/or the main lumen may function as the fluid injection lumen or the fluid return lumen. If the ablation catheter includes thermoelectric cooling elements or electrodes capable of transmitting radiofrequency (RF) (as shown in FIGS. 1A-5B), ultrasound, microwave, electroporation energy, or the like, the elongate body 18 may include a lumen in electrical communication with an energy generator 62.

The console 14 may be in electrical and fluid communication with the medical device 12 and include one or more fluid (such as coolant or saline) reservoirs 59, fluid return reservoirs 60, energy generators 62 (for example, an RF or electroporation energy generator), and computers 64 with displays 66, and may further include various other displays, screens, user input controls, keyboards, buttons, valves, conduits, connectors, power sources, processors, and computers for adjusting and monitoring system 10 parameters. The computer 64 may include one or more processors that are in electrical communication with the one or more system components for controlling energy application and/or duration, performing mapping functions, and/or comparing patient or system measurements to threshold measurements to ensure patient safety and/or the delivery of efficient treatment.

Referring now to FIG. 1D, a close-up view of the point of connection between the first and second arms and the shaft is shown. As described regarding FIGS. 1A-1C, The proximal end 52, 54 of each arm 30, 32 may be secured within the distal portion 20 of the elongate body 18. As a non-limiting example, the proximal end 52, 54 of each arm 30, 32 may be coupled to a cuff 56 having an aperture through which the shaft 36 may be extended, retracted, and rotated. Extending the shaft 36 from the distal portion 20 of the elongate body 18 will likewise extend the arms 30, 32, causing them to lie flat against the shaft 36 (not shown), or will at least cause the electrodes 24 to lie along an axis that is substantially parallel to the device longitudinal axis 26 (as shown in FIG. 1B). Rotation of the shaft 36 does not move the proximal end 52, 54 of each arm 30, 32, but may rotate the distal end 46, 48 of each arm 30, 32, thereby putting a helical or semi-helical twist in each arm 30, 32 about the shaft 36. The degree of twisting may depend on the degree of rotation of the shaft 36 (as shown and described in FIGS. 2-4).

Figure 2:
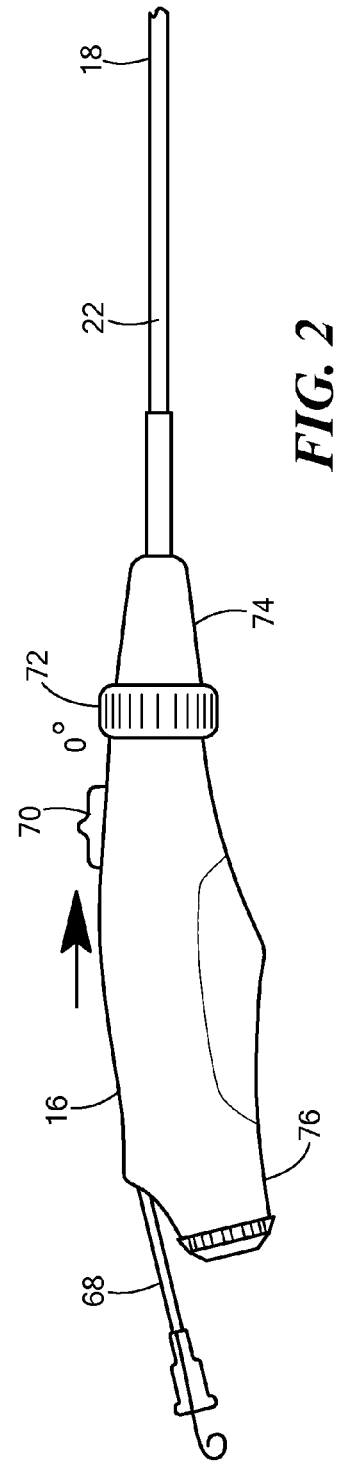
FIG. 2 shows a steering mechanism configuration that results in the distal portion having a first (linear) configuration.

Referring now to FIG. 2, a steering mechanism configuration that results in the distal portion having a first (linear) configuration is shown. The proximal portion 22 of the elongate body 18 may be coupled to the handle 16. Additionally, a proximal portion 68 of the shaft 36 may be in mechanical communication with one or more actuation elements within the handle 16. For example, as shown in FIG. 2, the shaft 36 may be extended and retracted by a slide knob 70 and may be rotated by a rotational knob 72. When the electrode array 28 is in the linear configuration (as shown in FIGS. 1A-1C), the slide knob may be fully advanced toward the distal end 74 of the handle 16 and the rotational knob 72 may be in the neutral position (0° rotation).

Figure 1E:
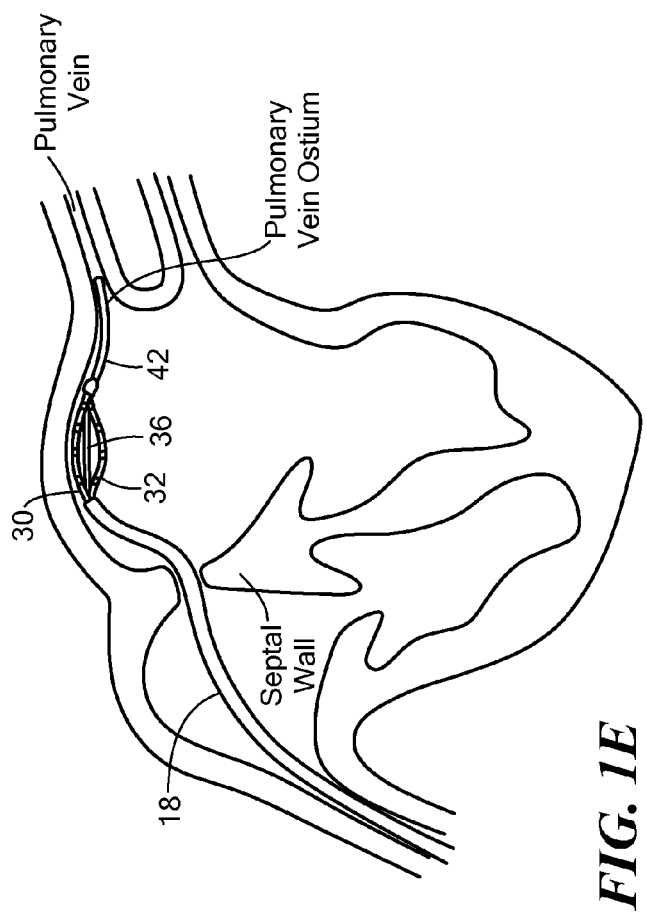
FIG. 1E shows a device having an adjustable electrode array in a linear configuration being used to ablate cardiac tissue.

When the electrode array 28 is in the linear configuration, the device 12 may be suitable for creating linear lesions (as shown in FIG. 1E). Linear lesions may be desirable when the aberrant electrical activity occurs in the heart wall, such as the wall of the right or left atrium, or if a roof-line ablation is performed (that is, a linear ablation between the left and right superior pulmonary veins). Additionally, the over-the-wire design of the device 12 may allow the device 12 to be anchored within the left superior pulmonary vein during a roof-line ablation procedure. Further, when the electrode array 28 is transitioned to other configurations, the same device 12 may also be used to treat other areas of the heart, such as the pulmonary vein ostia and septum (as shown in FIGS. 3D and 3E).

Figure 3A:
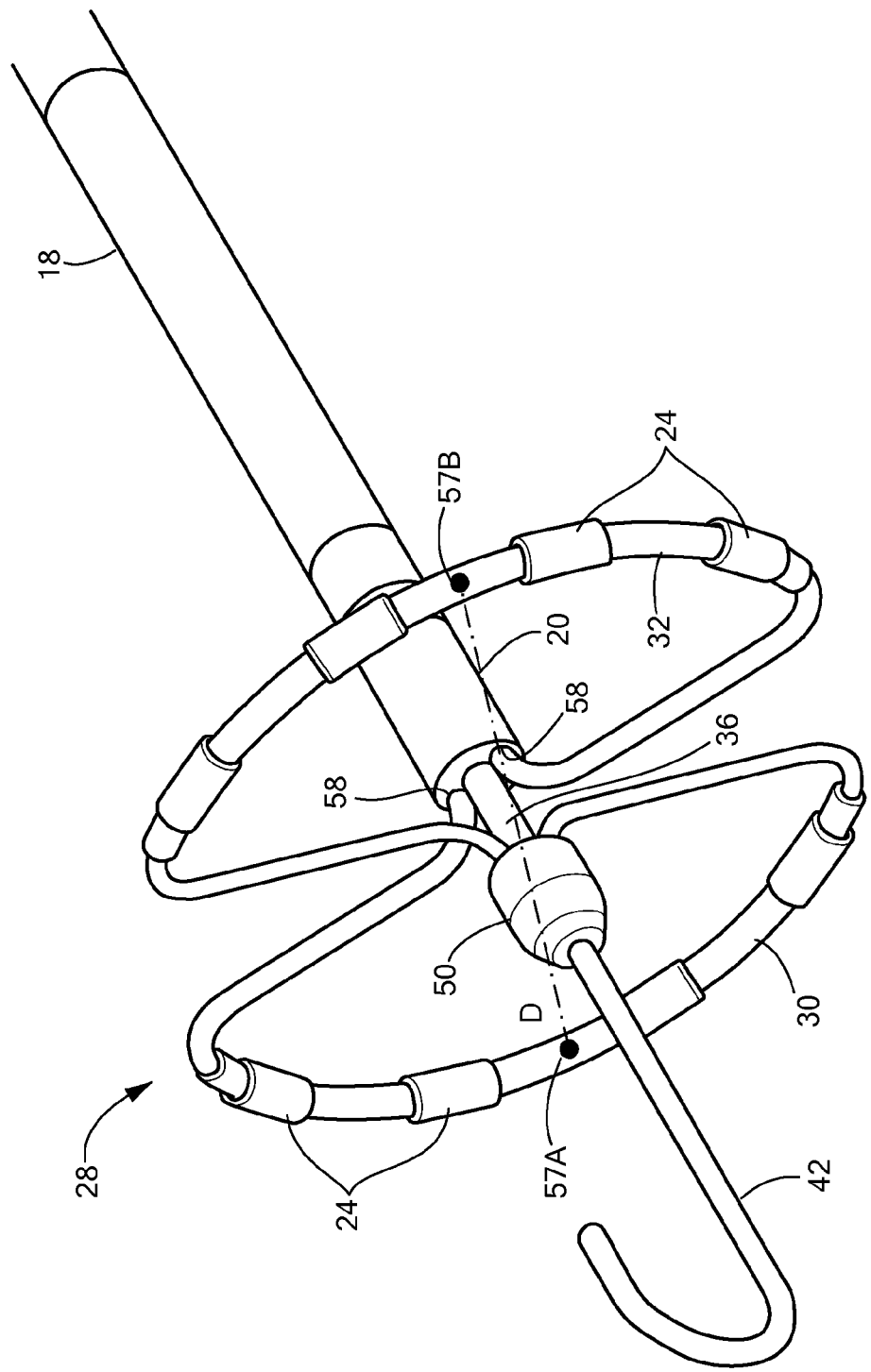
FIG. 3A shows a first view of a device distal portion with an adjustable electrode array in a second (radially expanded) configuration.
Figure 3B:
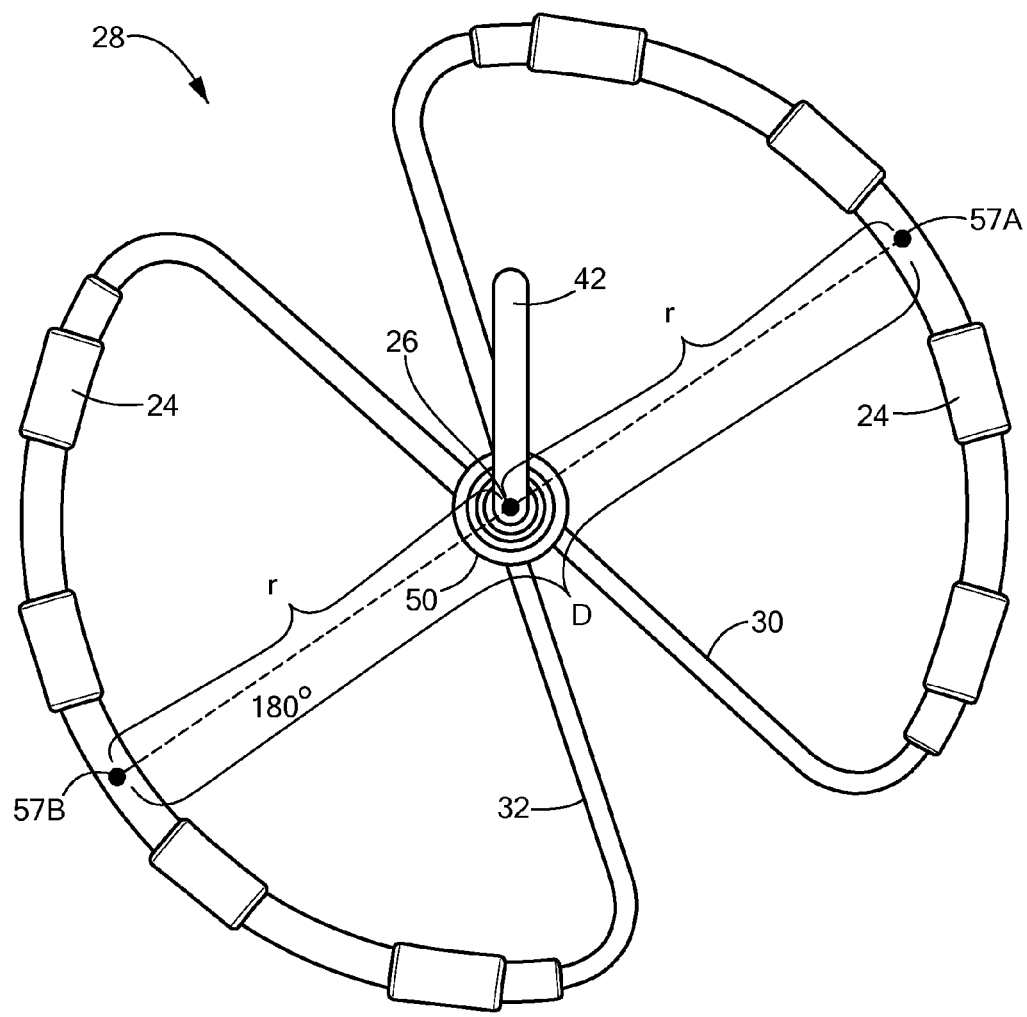
FIG. 3B shows a second view of a device distal portion with an adjustable electrode array in a second (radially expanded) configuration.
Figure 3C:
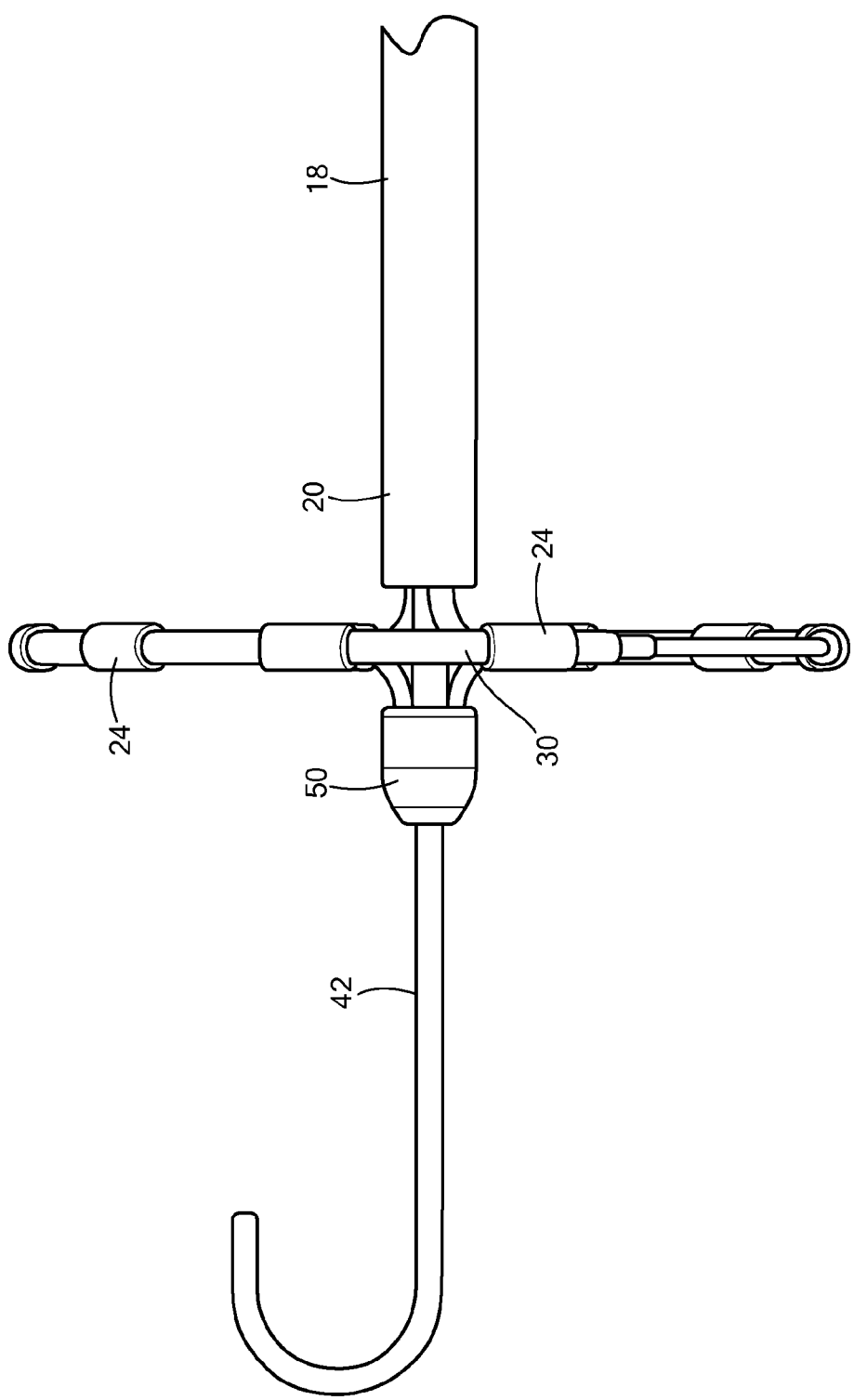
FIG. 3C shows a third view of a device distal portion with an adjustable electrode array in a second (radially expanded) configuration.
Figure 3D:
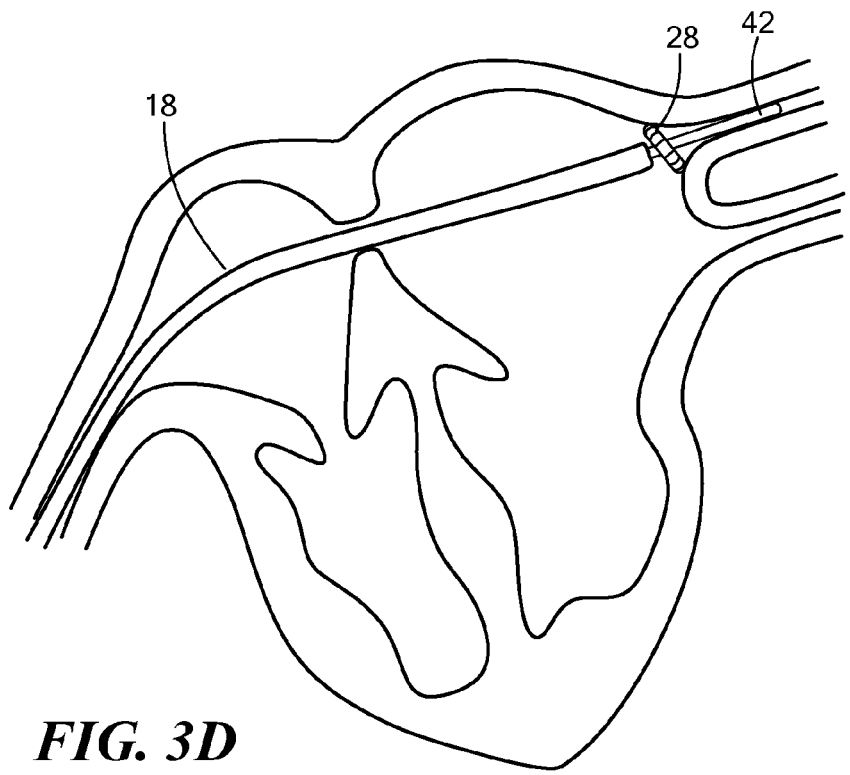
FIG. 3D shows a device having an adjustable electrode array in a radially expanded configuration being used to ablate a pulmonary vein ostium.
Figure 3E:
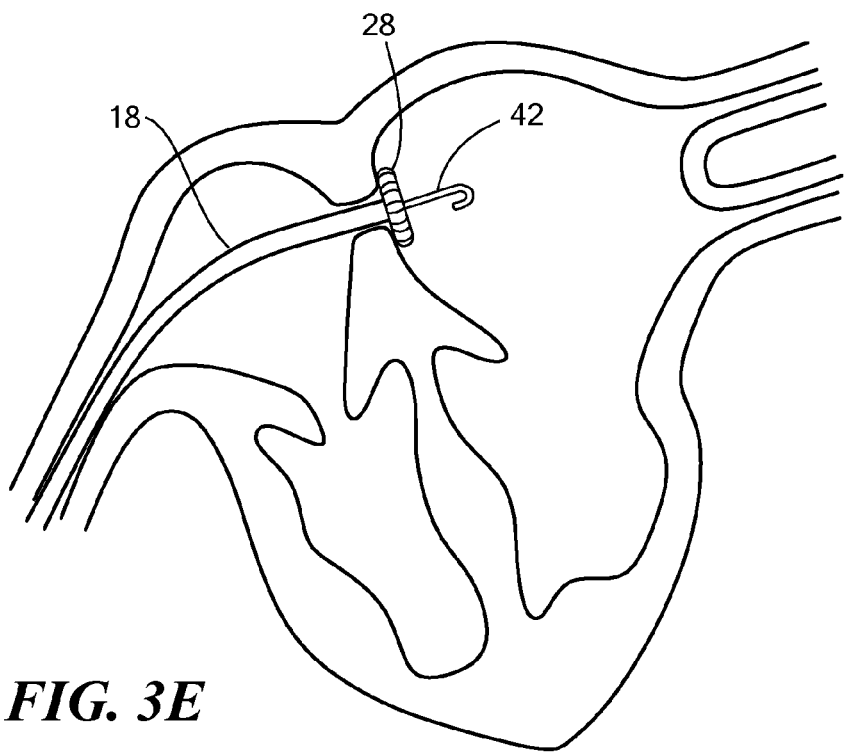
FIG. 3E shows a device having an adjustable electrode array in a radially expanded configuration being used to ablate a septal wall.

Referring now to FIGS. 3A-3C, a device distal portion with an adjustable electrode array in a second (radially expanded) configuration is shown. When the shaft 36 is rotated and retracted, the distal cap 50 and distal end 46, 48 of each arm 30, 32 are brought toward the distal portion 20 of the elongate body 18 and the arm proximal ends 52, 54, and the arms 30, 32 are slightly twisted about the shaft 36. As a result, the electrode array 28 transitions from a linear configuration to a radially expanded configuration, in which each arm 30, 32 has an arcuate shape (that is, bowing out in a direction that is approximately 180° from the other arm). This configuration is clearly seen in the anterior view of FIG. 3B. Further, when the electrode array 28 is in the radially expanded configuration, the two arms 30, 32 may be coplanar and lie in a plane that is substantially orthogonal to the device longitudinal axis 26 (as shown in FIG. 3C). In the radially expanded configuration, the midpoints 57A, 57B may be approximately 180° from each other along a line (referred to in FIGS. 3A, 3B, 5A, and 5B as line "D") that is in the plane in which the arms 30, 32 lie, substantially orthogonal to the device longitudinal axis 26.

Additionally, the midpoints 57A, 57B are each located a radial distance (referred to in FIG. 3B as "r") from the longitudinal axis 26.

Figure 4:
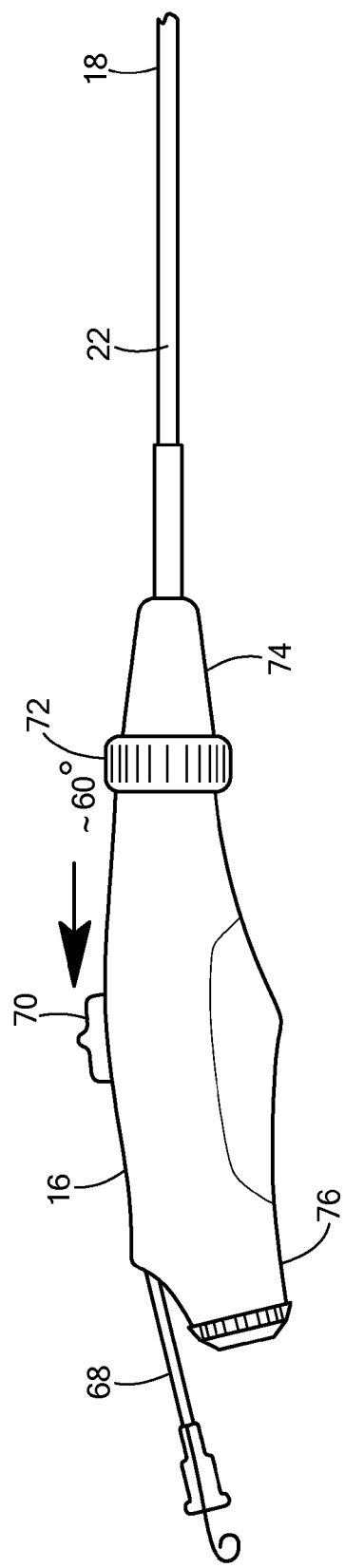
FIG. 4 shows a steering mechanism configuration that results in the distal portion having a second (radially expanded) configuration.

Referring now to FIG. 4, a steering mechanism configuration that results in the distal portion having a second (radially expanded) configuration is shown. In the radially expanded configuration, the device 12 may be suitable for creating circumferential lesions, such as when ablating pulmonary vein ostia or an inner diameter of a hollow anatomical structure (for example, a pulmonary vein). Additionally, in this configuration the device 12 may be used to ablate the septum (as shown in FIG. 3E). As shown and described in FIG. 3C, when in the radially expanded configuration the arms 30, 32 may lie in a plane that is substantially orthogonal to the device longitudinal axis 26, and this lends strength to the electrode array 28 when the array 28 is pulled back against the septum. That is, the arms 30, 32 will not be inadvertently bent toward the distal cap 50, as could occur in ablation devices that have an electrode array that is canted toward the distal tip of the device.

When the electrode array 28 is in the radially expanded configuration (as shown in FIGS. 3A-3C), the slide knob may be fully retracted toward the proximal end 16 of the handle 16 and the rotational knob 72 may be rotated by an angle between approximately 45° and approximately 90° (for example, 60°) in a clockwise or counterclockwise direction. However, any degree of rotation may be used, depending on the desired diameter Referring now to FIGS. 5A and 5B, anterior views of an adjustable electrode array in a second (radially expanded) configuration and at least a third (increased-diameter radially expanded) configuration are shown for comparison. The diameter $D_2$ of the electrode array 28 between the midpoint 57A, 57B of each arm 30, 32 in the increased-diameter radially expanded configuration (as shown in FIG. 5B) may be greater than the diameter $D_1$ of the electrode array 28 between the midpoint 57A, 57B of each arm 30, 32 in the radially expanded configuration (FIG. 5A). It will be understood that the electrode array 28 may be adjustable to have any of a range of diameters other than those shown in FIGS. 5A and 5B, depending on the degree of shaft 36 rotation. Depending on the size of the radius, the electrode array 28 may optionally be used to perform a first ablation, rotated approximately 90°, and used to perform a second ablation in order to create a fully circular lesion. Additionally, not only is the diameter of the electrode array 28 adjustable, but electrode 24 symmetry about the shaft 36 is preserved regardless of the diameter of the electrode array 28. That is, the arms 30, 32 are symmetrically positioned about the longitudinal axis 26, the distance between the longitudinal axis 26 and the midpoint 57A, 57B of each arm being equidistant. In both configurations shown in FIGS. 5A and 5B, the electrode array 28 may appear to have a lobed shape, with each lobe comprising an arm 30, 32. The lobes are separated by an angle α. As the radial distance between the midpoint 57A, 57B of each the arms 30, 32 and the longitudinal axis 26 increases, the angle α between the lobes also increases. The first angle α (in FIG. 5A) is referred to as $α_1$ and the second angle α (in FIG. 5B) is referred to as $α_2$. An adjustable radius may be particularly useful for accommodating a variety of pulmonary vein diameters. The first radius r (in FIG. 5A) is referred to as $r_1$ and the second, increased radius (in FIG. 5B) is referred to as $r_2$. Thus, the device 12 may not only perform the function of linear and septal ablation catheters, but may also perform the function of, and improve upon, multiple types of pulmonary vein ostia ablation catheters.

To achieve the increased-diameter configuration, the shaft 36 may be retracted and rotated so that the distal cap 50 is brought toward the elongate body distal portion 20, similar to the method for transitioning the electrode array 28 to the radially expanded configuration. However, the shaft 36 may be rotated less than approximately 45°, thus causing the arms 30, 32 to bow out at a greater degree of curvature (that is, causing each arm 30, 32 to form a lobe with a midpoint 57A, 57B that is a greater radial distance from the longitudinal axis 26) than when the shaft is rotated approximately 45° or more. This greater degree of curvature translates to a greater electrode array 28 radius.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, the medical device comprising:
an elongate body defining a longitudinal axis, a proximal portion, and a distal portion;
a shaft rotatably and slidably disposed within the elongate body, the shaft defining a distal portion and a proximal portion and being configured to rotate within the elongate body;
a treatment array including a first arm defining a distal end engaged with the shaft distal portion, a proximal end engaged with the elongate body distal portion, and a first midpoint at a first position, and a second arm defining a distal end engaged with the shaft distal portion, a proximal end engaged with the elongate body distal portion, and a second midpoint at a second position,
the rotation of the shaft relative to the elongate body about the longitudinal axis and movement of the shaft along the longitudinal axis together being configured to transition the treatment array from a first configuration to a second configuration, the movement of the shaft along the longitudinal axis being configured to transition each of the first arm and the second arm from a substantially linear shape to an arcuate shape, and the rotation of the shaft relative to the elongate body about the longitudinal axis being configured to cause the first arm and the second arm to be positioned such that the first arm and the second arm are coplanar with each other in a plane that is substantially orthogonal to the longitudinal axis with the first and second midpoints being approximately 180° from each other.

2. The medical device of claim 1, further comprising a first plurality of electrodes on the first arm and a second plurality of electrodes on the second arm.

3. The medical device of claim 2, wherein the first and second plurality of electrodes are configured to have a radial symmetry about the longitudinal axis when the treatment array is in the radially expanded configuration.

4. The medical device of claim 3, wherein the distal portion of the shaft is configured to extend beyond the distal portion of the elongate body.

5. The medical device of claim 4, wherein the medical device further includes a distal cap engageable with the distal portion of the shaft and the distal end of each of the first arm and the second arm, each of the first midpoint and the second midpoint is equidistant from the distal cap and the distal portion of the elongate body.

6. The medical device of claim 5, wherein the first midpoint and the second midpoint are each separated from the longitudinal axis by a radial distance.

7. The medical device of claim 6, wherein the rotation of the shaft relative to the elongate body about the longitudinal axis without further retraction of the shaft when the treatment array is in the radially expanded configuration is adapted to adjust the radial distance of the first midpoint and the second midpoint from the longitudinal axis from a first radial distance to a second radial distance.

8. The medical device of claim 7, wherein the rotation of the shaft relative to the elongate body between approximately 45° and approximately 90° is configured to cause the first and second midpoints to be the first radial distance from the longitudinal axis.

9. The medical device of claim 8, wherein the rotation of the shaft relative to the elongate body approximately 60° is configured to cause the first and second midpoints to be the first radial distance from the longitudinal axis.

10. The medical device of claim 7, wherein the radial distance of the first midpoint from the longitudinal axis is substantially the same as the radial distance of the second midpoint from the longitudinal axis.

11. The medical device of claim 10, wherein the proximal portion of the elongate body is coupled to a handle including a rotational knob, and the proximal portion of the shaft is in communication with the rotational knob.

12. The medical device of claim 7, wherein the rotation of the shaft relative to the elongate body less than approximately 45° is configured to cause the first and second midpoints to be the second radial distance from the longitudinal axis, the second radial distance being greater than the first radial distance.

13. The medical device of claim 1, wherein the medical device further comprises a guidewire slidably disposed within the shaft.

14. A medical device for treating multiple anatomical areas of a patient's body, the medical device comprising:
    an elongate body having a distal portion, a proximal portion, and a longitudinal axis;
    a first arm and a second arm each coupled to the distal portion of the elongate body, the first arm and the second arm each having a distal end, a proximal end, a length extending between the distal end and the proximal end, and a midpoint, the first arm including a first plurality of electrodes and the second arm including a second plurality of electrodes, the midpoint of the first arm being between two of the first plurality of electrodes and the midpoint of the second arm being between two of the second plurality of electrodes,
    retraction of the distal ends of each of the first arm and the second arm toward the proximal end of each of the first arm and the second arm are configured to transition the length of each of the first arm and the second arm from a linear configuration to an arcuate, radially expanded configuration and rotation of the distal ends of the first arm and the second arm relative to the elongate body after the retraction of the distal ends is adapted to configure the first arm and the second arm such that the length of each of the first arm and the second arm are coplanar with each other in a plane that is substantially orthogonal to the longitudinal axis of the elongate body with the midpoints of the first and second arms being approximately 180° from each other.

15. The medical device of claim 14, wherein each electrode of each of the first and the second plurality of electrodes is equidistant from the longitudinal axis of the elongate body in different radial directions when the device is in the arcuate, radially expanded configuration.

16. The medical device of claim 15, wherein the arcuate, radially expanded configuration has a diameter that is adjustable from a first diameter to at least a second diameter, each electrode of each of the first and second plurality of electrodes is equidistant from the longitudinal axis of the elongate body in different radial directions when the arcuate, radially expanded configuration has the first diameter and when the arcuate, radially expanded configuration has the at least second diameter.

17. A method for treating multiple locations within a patient's heart, the method comprising:
    positioning a medical device within the patient's heart, the medical device comprising an elongate body defining a longitudinal axis, a proximal portion and a distal portion and a shaft rotatably and slidably disposed within the elongate body, the shaft defining a distal portion and a proximal portion; and
    transitioning a distal end of the medical device from a linear configuration to a radially expanded configuration by retracting and rotating the shaft within and relative to the elongate body, the distal end of the medical device including a first arm having a distal end coupled to the distal portion of the shaft and a proximal end coupled to the distal portion of the elongate body and having a length extending from the distal end to the proximal end, a first plurality of electrodes, and a first midpoint, and a second arm having a distal end coupled to the distal portion of the shaft and a proximal end coupled to the distal portion of the elongate body and having a length extending from the distal end to the proximal end, a second plurality of electrodes, and a second midpoint, the length of the first arm and the length of the second arm each lying along an axis that is parallel to the medical device longitudinal axis when the distal end of the medical device is in the linear configuration, and the length of the first arm and the length of the second arm being coplanar with each other and lying in a plane that is orthogonal to the elongate body's longitudinal axis with the first midpoint and the second midpoint being located approximately 180° from each other when the distal end of the medical device is in the radially expanded configuration.

18. The method of claim 17, wherein the radially expanded configuration is adjustable between having a first diameter and having a second diameter.

19. The method of claim 18, wherein the method further comprises activating the first and second plurality of electrodes and at least one of:
    creating a linear ablation lesion on the cardiac wall tissue;
    creating a circumferential ablation lesion on the cardiac wall tissue;
    creating a circumferential ablation lesion about a pulmonary vein ostium;
    creating a circumferential ablation lesion about a pulmonary vein antrum;
    creating a circumferential ablation lesion within a pulmonary vein; and
    creating a lesion on cardiac septal wall tissue.

* * * * *